United States Patent [19]

Tissier et al.

[11] Patent Number: 5,186,040

[45] Date of Patent: Feb. 16, 1993

[54] METHOD FOR MEASURING THE VISCOSITY OF A MATERIAL

[75] Inventors: Annie Tissier, Saint Ismier; Jean-Francois Teissier, Voiron, both of France

[73] Assignee: France Telecom (CNET), Paris, France

[21] Appl. No.: 798,090

[22] Filed: Nov. 27, 1991

[30] Foreign Application Priority Data

Nov. 29, 1990 [FR] France .................... 90 15241

[51] Int. Cl.$^5$ ............................................ G01N 11/00
[52] U.S. Cl. .................................................. 73/54.01
[58] Field of Search ......................... 73/54.41, 54.01; 356/354

[56] References Cited

U.S. PATENT DOCUMENTS

| | | | |
|---|---|---|---|
| 4,188,123 | 2/1980 | Kleinknecht | 356/354 |
| 4,813,781 | 3/1989 | Tissier et al. | 356/354 |

OTHER PUBLICATIONS

A. Tissier et al.: "Glass Reflow Modeling for Process Optimization", Proceedngs of the 17th European Solid State Device Research Conference, Sep., 1987, pp. 431-434.

A. Tissier et al, "An Optical Method for In-Line Glass Flow Control", Proceedings of the SPIE, vol. 1012, Sep. 1988, pp. 186-193.

*Primary Examiner*—Hezron E. Williams
*Assistant Examiner*—Joseph W. Roskos
*Attorney, Agent, or Firm*—Lowe, Price, LeBlanc & Becker

[57] ABSTRACT

A method for measuring the viscosity of a material consists in forming an array of parallel strips of material for constituting a diffraction grating; illuminating the array with a monochromatic light beam which produces a diffraction grating comprised of a main light spot (5) and of a plurality of adjacent diffraction spots, the envelope of which exhibits a major lobe (LO) including the main spot (5) and minor lobes (L1, L2); subjecting the array to a thermal process consisting in rapidly heating it at a predetermined temperature (T) and maintaining it at such temperature; selecting the brightest spot (6) among those of the first lobe (L1) and measuring the evolution of its light intensity (HL1) during the thermal process; determining the time interval elapsing until the first passage by a minimum intensity value (HL1b) of the spot (6); and deducting therefrom the value ($v$) of the viscosity of the material constituting the array by the formula $1/v = \alpha d$.

2 Claims, 2 Drawing Sheets

METHOD FOR MEASURING THE VISCOSITY OF A MATERIAL

BACKGROUND OF THE INVENTION

The present invention relates to a method for measuring the viscosity of a thin-layer material deposited on a substrate.

The invention especially relates to the field of integrated circuits. During manufacturing of integrated circuits, determined materials have to be deposited in very thin layers and the shape of these thin layers has to be modified by appropriate thermal processes that cause the material to flow. The flowing of the material corresponds to a mass transfer resulting from superficial forces, this mass transfer being possible only if the material has a determined viscosity.

Generally, the materials that are deposited in thin layer are not intended to be heated at high temperatures for a sufficiently long time to provide a very substantial flowing. It is simply tried to change, by a determined flowing, the shapes of the patterns of the deposited material, particularly to round up angles. During manufacturing of integrated circuits, a thermal process aiming at achieving a determined flowing of a given material can be properly carried out only if the viscosity of the material, at the selected temperature, is relatively well known. Particularly, the knowledge of this viscosity can serve as a parameter introduced in modelling systems which are constituted by softwares enabling to foresee the behavior and arrangement of microstructures, without involving a high number of actual experiments. Also, it may be advantageous to very accurately know the viscosity of a determined material, at a given temperature, for any other reason than that mentioned above.

The structure and chemical compositions of materials in thin layers do not strictly correspond to that of the corresponding bulk material. Hence, it is not possible to deduce, by conventionally measuring a bulk viscosity, the viscosity of the same material deposited in thin layer.

It is reminded that the measurement of viscosity according to conventional methods consists in disposing a determined amount of material in a tank provided with an aperture and measuring the flowing rate of this material through the aperture.

U.S. Pat. No. 4,813,781 teaches that it is possible to measure the degree of flowing of a material deposited in thin layer by forming on a substrate an array of parallel strips of the material, so that these parallel strips constitute a diffraction grating, by subjecting the grating to the conditions wherein the material flows, by lighting the grating with a monochromatic light beam and by observing the evolution of the light diffracted during flowing. Particularly, the intensity of at least one light spot of the diffracted pattern is measured and a determined distortion level of the pattern strips is deduced therefrom and, hence, a determined flowing value.

This method enables comparing a flowing level of a material to an equal flowing level of the same material previously obtained and which was satisfactory. However, this method does not enable to quantitatively measure the displacements of materials and hence does not enable to determine, for given conditions, the viscosity index of a material.

SUMMARY OF THE INVENTION

An object of the invention is to provide a simple and reliable method for measuring the viscosity of a thin layer of a material.

To achieve this object, the invention provides a method for measuring the viscosity of a material consisting in forming an array of parallel strips of the material for constituting a diffraction grating; illuminating the array with a monochromatic light beam, the diffracted light of which provides a diffraction grating comprised of a main light spot corresponding to the specular reflection and a plurality of adjacent, aligned, diffraction spots, the envelope of which exhibits a major lobe including the main spot and minor lobes among which the first lobe is adjacent to the major lobe; subjecting the pattern to a thermal process consisting in rapidly heating it at a predetermined temperature and maintaining it at this temperature; selecting the brightest spot among those of the first lobe and measuring the evolution of the light intensity of the spot during the thermal process; determining the time interval d elapsing until the first passage through a minimum intensity value of the spot; and deducting therefrom the value $v$ of the viscosity of the material constituting the pattern by the formula $1/v = \alpha d$, where $\alpha$ is a constant determined by calibration of the apparatus with a known material.

Preferably, the parallel strips of the diffraction grating are regularly spaced and each exhibits a cross section in the form of a rectangle having a width $\zeta$ and a thickness e, and are separated by a pitch p, the light beam has a wavelength $\lambda$. Values $\zeta$, e and $\lambda$ meet the following criteria:

$$1 \, \mu m < \zeta < 60 \, \mu m$$

$$0.1 \, \mu m < e < 6 \, \mu m$$

$$0.2 \, \mu m < \lambda < 10 \, \mu m,$$

and the ratio $p/\zeta$ is such that the number of spots of the first lobe is higher than 4.

BRIEF DESCRIPTION OF THE DRAWINGS

The foregoing and other objects, features and advantages of the invention will be apparent from the following detailed description of a preferred embodiment as illustrated in the accompanying figures wherein.

DETAILED DESCRIPTION OF THE INVENTION

Figure 2:
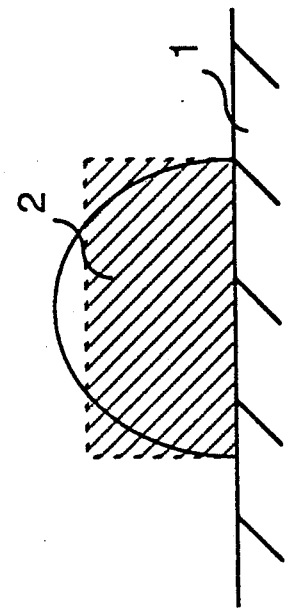
FIG. 2 is a schematic cross-section view of one of the parallel strips constituting the diffraction grating shown in FIG. 1.

The method for measuring the viscosity according to the invention involves, first of all, the formation on a plate 1 of a diffraction grating constituted by an assembly of parallel strips 2 regularly spaced apart, made in the material, the viscosity of which is to be measured at a determined temperature T. The cross section of each strip 2 is rectangular, as shown in FIG. 2.

If plate 1, and consequently the parallel strips 2, is heated at a determined temperature T, the viscosity of the material at this temperature T becomes sufficiently low so that the forces resulting from the superficial stress cause a distortion of parallel strips 2.

Figure 3:
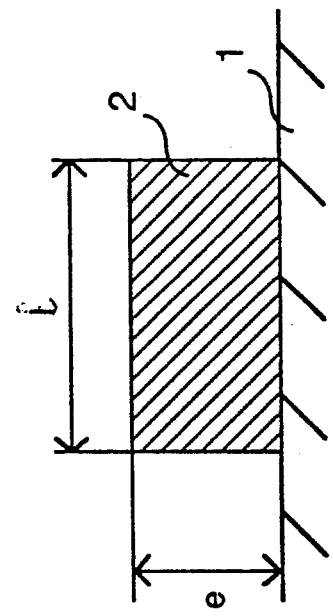
FIG. 3 is a schematic cross-section view of the same element as that of FIG. 2 having been subject to flowing.

FIG. 3 shows a parallel strip 2 which has been subject to a determined flowing. It can be seen that the shapes are rounded up. If, at temperature T, the viscosity is extremely low or if, which gives an equivalent result, the sample is heated at this temperature for a very long time, the initial rectangular shape (FIG. 2) tends to become a flattened spheric shape corresponding to the shape of a drop of water on a plane surface.

According to the invention, the diffraction grating constituted by parallel strips 2 is subject to a thermal processing consisting in rapidly heating the diffraction grating at a predetermined temperature T. During the thermal process, the diffraction grating is illuminated by a monochromatic light beam having a wavelength in the range of visible, ultraviolet or infrared radiations.

Figure 4A:
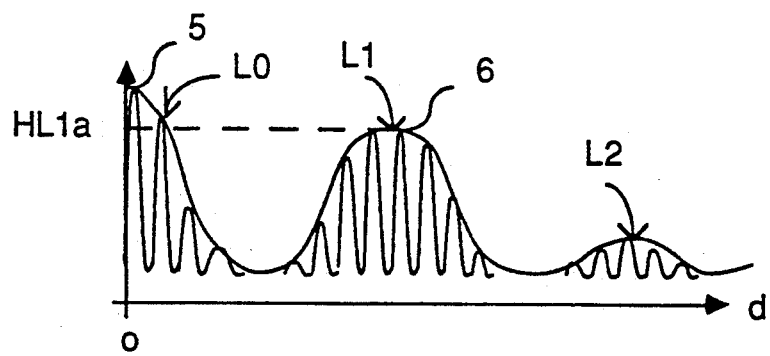
FIGS. 4A, 4B and 4C show the diffraction diagram obtained by implementing the method according to the invention, during three successive flowing steps of the material.

The diffraction light provides a diffraction grating, an example of which is shown in FIG. 4A. This diffraction grating is composed of a main light spot 5 corresponding to the specular reflection and a plurality of adjacent, aligned, diffraction spots, the envelope of which exhibits a major lobe L0 including the main spot 5 and minor lobes L1, L2, etc., among which the first lobe L1 is adjacent to the major lobe L0. FIG. 4A shows only half of the diffraction grating as it is symmetrical with respect to the specular plane.

The applicant has studied this diffraction grating and its evolution during flowing which is continuously achieved when the sample is heated at a constant temperature T, in order to provide an accurate and reproducible method for measuring the actual value of the material viscosity at temperature T.

Figure 4B:
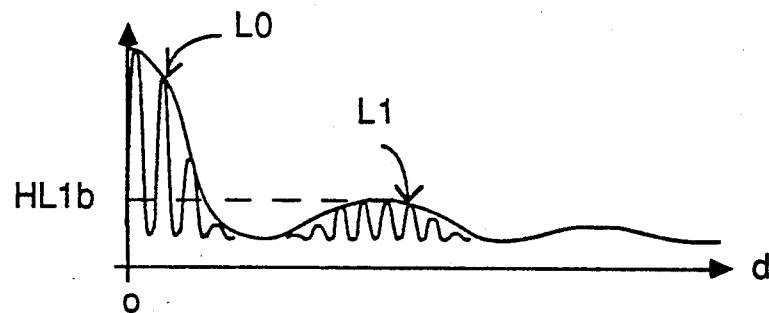
Figure 4C:
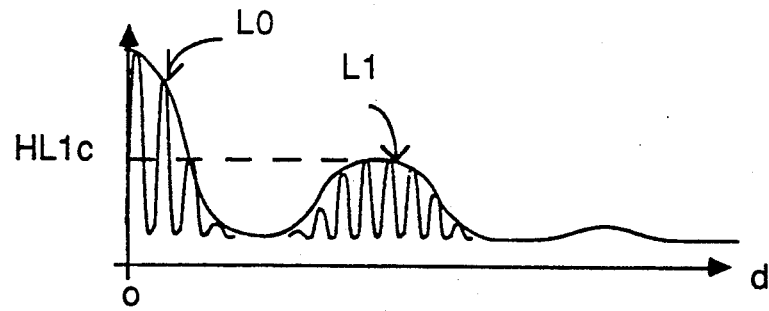

According to the invention, the brightest spot 6 among those of the first lobe L1 is selected and the evolution of the light intensity HL1 of spot 6 during the thermal process is measured. When the thermal process of the sample is started, at time $t_0$, a determined diffraction grating is obtained, some time is allowed to elapse and, at time ta, another diffraction grating corresponding to FIG. 4A is obtained. At a subsequent time tb, another diffraction grating corresponding to FIG. 4B is obtained, and at a later time tc, a diffraction grating corresponding to FIG. 4C is obtained. In fact, the shape of the diffraction grating remains substantially equal during the progressive flowing of the sample, but the applicant has noticed that the light intensity HL1 of the brightest spot 6 of the first lobe L1 varies in a relatively substantial way as a function of the evolution of the pattern flowing during thermal process.

Figure 5:
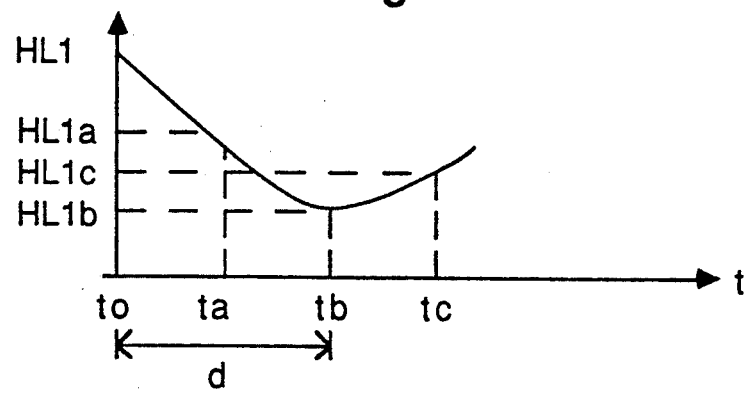
FIG. 5 is a curve showing the relationship between the degree of flowing and the parameter HL1 used in the method according to the invention.

FIG. 5 shows the evolution of the light intensity HL1 of spot 6 during flowing. At time ta, the light intensity of spot 6 has a relatively high value HL1a; at the subsequent time tb, the intensity takes a substantially lower value HL1b; and at the later time tc, it can be seen that value HL1c is again higher than value HL1b.

Thus, the patent applicant has noticed that, during flowing, the light intensity HL1 of spot 6 starts decreasing, passes through a minimum value HL1b, then increases again. Now, it is very easy to view or to calculate with automatic apparatuses the time when the value of a light intensity goes through a minimum.

This passage by a minimum value is specific of the brightest spot of the first lobe and can be univocally associated with the distortion state of the diffraction grating strips. Hence, the time interval d between time $t_0$ corresponding to the beginning of the thermal process and time tb is a physical value representative of the value of the viscosity of the material constituting the diffraction grating at temperature T at which the pattern is heated. In fact, this time interval d is reversely proportional to the value of viscosity, the proportionality coefficient being liable to be determined by previous calibration carried out with a material, having a known viscosity when deposited in thin layer.

When implementing the method for measuring the viscosity according to the invention for the first time on a determined equipment, it is necessary, first of all, to calibrate it by forming a first array of a material having a known viscosity $v0$ and by measuring, as above described, the time interval d0 elapsed between time $t_0$ at the beginning of the thermal process and time tb. Then, a constant $\alpha$ is determined from the following formula:

$$1/v0 = \alpha d0.$$

The viscosity measurement that is subsequently carried out is made from a diffraction grating 2 having a geometrical shape and dimensions strictly identical to the first array but formed in the material, the viscosity of which is to be measured. Measurement of time interval d is achieved on this pattern and the viscosity index $v$ is deducted by the following formula:

$$1/v = \alpha d,$$

coefficient $\alpha$ having been previously determined as indicated above.

Figure 1:
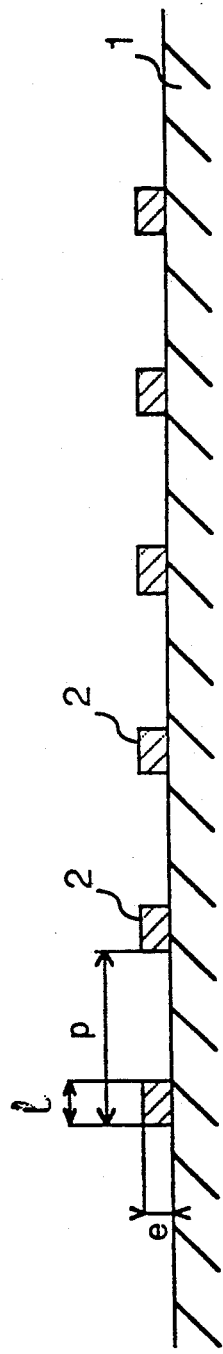
FIG. 1 is a schematic cross-section view of a diffraction grating used for implementing the method according to the invention.

According to another aspect of the invention, the diffraction grating has to meet some size requirements so that the above described method for measuring the viscosity enables a reliable and reproducible determination of the value of the material viscosity. FIGS. 1 and 2 will be referred to for explaining these requirements. Each parallel strip 2 has a rectangular-shaped cross-section having a width $\zeta$ and a thickness e. Also, p defines the pitch of the pattern, that is, the distance separating lateral edges corresponding to two adjacent parallel strips 2. The wavelength of the monochromatic light beam is $\lambda$.

For the selected wavelength $\lambda$, it is necessary to choose $\zeta$ and e values which are such that the obtained diffraction grating has a first lobe L1 sufficiently high and that the light intensity HL1 actually varies, as a function of flowing, reaching a minimum at a precise time ta. It is also necessary to choose a value for e corresponding to the order of magnitude of the thickness of the layers it is desired to subsequently achieve with the material, the viscosity of which is to be measured.

Thus, according to an embodiment of the invention, for a wavelength $\lambda$ ranging from 10 to 0.2 $\mu$m, values $\zeta$ and e meet the following criteria:

$$1\ \mu m < \zeta < 60\ \mu m$$

$$0.1\ \mu m < e < 6\ \mu m.$$

Still for the selected wavelength λ, it is also necessary to choose a ratio p/ζ such that the number of spots of the first lobe L1 of the diffraction grating is higher than 4.

Some materials, the viscosity of which is to be measured cannot be easily etched. In that case, it is too difficult or impossible to achieve with such materials a satisfactory diffraction grating. To overcome this difficulty, a diffraction grating is achieved on a plane substrate, this pattern being similar to the one above described but being made of a material, the etching of which is well known, and which will not, or very little, flow at the measurement temperature T. Then, on this pattern, a thin layer of the material to be analyzed is deposited. This layer thus takes the shape of the underlying pattern and constitutes in turn the diffraction grating used for measuring the viscosity according to the invention.

We claim:

1. A method for measuring the viscosity of a material comprising the following steps:
   forming an array of parallel strips (2) of said material for constituting a diffraction grating;
   illuminating the array with a monochromatic light beam, the diffracted light of which produces a diffraction grating comprised of a main light spot (5) corresponding to the specular reflection and of a plurality of adjacent, aligned, diffraction spots, the envelope of which exhibits a major lobe (L0) including said main spot (5) and minor lobes (L1, L2) among which said first lobe (L1) is adjacent to said major lobe (L0);
   subjecting said array to a thermal process consisting in rapidly heating it at a predetermined temperature (T) and maintaining it at said temperature;
   selecting the brightest spot (6) among those of said first lobe (L1) and measuring the evolution of the light intensity (HL1) of said spot (6) during the thermal process;
   determining the time interval (d) elapsing until the first passage by a minimum intensity value (HL1b) of said spot (6); and
   deducing therefrom the value (ν) of the viscosity of the material constituting the array by the formula $1/\nu = \alpha d$, where $\alpha$ is a constant determined by calibration of the apparatus with a known material.

2. A method for measuring the viscosity of a material according to claim 1, wherein the parallel strips (2) of the diffraction grating are regularly spaced, each exhibiting a cross section in the form of a rectangle having a width ζ and a thickness e, and are separated by a pitch p, and wherein the light beam has a wavelength λ, wherein the values ζ, e and λ meet the following criteria:

$$1\ \mu m < \zeta < 60\ \mu m$$

$$0.1\ \mu m < e < 6\ \mu m$$

$$0.2\ \mu m < \lambda < 10\ \mu m,$$

and wherein the ratio p/ζ is such that the number of spots of said first lobe (L1) is higher than 4.

* * * * *